(12) United States Patent
Hu

(10) Patent No.: US 10,674,997 B2
(45) Date of Patent: Jun. 9, 2020

(54) ULTRASONIC TRACKING PROBE AND THE METHOD

(71) Applicant: Shaohua Hu, Flushing, NY (US)

(72) Inventor: Shaohua Hu, Flushing, NY (US)

(73) Assignee: Shaohua Hu, Flushing, NY (US)

( * ) Notice: Subject to any disclaimer, the term of this patent is extended or adjusted under 35 U.S.C. 154(b) by 453 days.

(21) Appl. No.: 14/822,701

(22) Filed: Aug. 10, 2015

(65) Prior Publication Data

US 2017/0043128 A1    Feb. 16, 2017

(51) Int. Cl.
*A61B 8/00* (2006.01)
*A61B 8/08* (2006.01)
*A61B 8/12* (2006.01)
*A61M 25/01* (2006.01)
*A61B 90/00* (2016.01)

(52) U.S. Cl.
CPC .......... *A61B 8/4254* (2013.01); *A61B 8/0841* (2013.01); *A61B 8/12* (2013.01); *A61B 8/4444* (2013.01); *A61B 8/4494* (2013.01); *A61B 2090/3929* (2016.02); *A61M 25/0108* (2013.01)

(58) Field of Classification Search
CPC ... A61B 8/4254; A61B 8/4444; A61B 8/4494; A61M 25/0108
See application file for complete search history.

(56) References Cited

U.S. PATENT DOCUMENTS

| | | | | |
|---|---|---|---|---|
| 5,582,171 A | * | 12/1996 | Chornenky | A61B 1/00183 600/425 |
| 5,797,849 A | * | 8/1998 | Vesely | A61B 5/0422 600/461 |
| 8,167,805 B2 | * | 5/2012 | Emery | A61B 50/13 600/437 |
| 2005/0222596 A1 | * | 10/2005 | Maschke | A61B 17/320725 606/159 |
| 2006/0122514 A1 | * | 6/2006 | Byrd | A61B 5/06 600/466 |
| 2007/0106156 A1 | * | 5/2007 | Altmann | A61B 8/12 600/437 |
| 2007/0213616 A1 | * | 9/2007 | Anderson | A61B 8/0833 600/448 |
| 2013/0303888 A1 | * | 11/2013 | Deladi | A61B 5/066 600/424 |
| 2014/0180078 A1 | * | 6/2014 | Nair | A61B 8/5261 600/425 |
| 2016/0183910 A1 | * | 6/2016 | Tahmasebi Maraghoosh | A61B 8/085 600/462 |
| 2016/0317232 A1 | * | 11/2016 | Vaillant | A61B 8/12 |
| 2016/0324501 A1 | * | 11/2016 | Vignon | A61B 8/0841 |
| 2017/0007202 A1 | * | 1/2017 | Peszynski | A61B 8/0883 |
| 2017/0007213 A1 | * | 1/2017 | Motoki | G01S 7/52079 |
| 2017/0172539 A1 | * | 6/2017 | Vignon | A61B 8/0841 |

* cited by examiner

Primary Examiner — Matthew F Desanto

(57) ABSTRACT

An ultrasonic medical system comprising a tracking probe and a catheter is used for tracking a target inside human body. The ultrasonic probe has additional ultrasound sensors embedded around its main transducer array. A catheter is built with ultrasound transmitters at its distal end and sends active sound signals during each probe scanning cycle. The probe sensors track the 3D position of the target catheter using triangulation principle. The target position is rendered in the 3D anatomic context defined by the ultrasound images.

6 Claims, 4 Drawing Sheets

ULTRASONIC TRACKING PROBE AND THE METHOD

U.S. PATENT CITATIONS

| Cited Patent | Publication Date | Applicant | Title |
| --- | --- | --- | --- |
| U.S. Pat. No. 5,029,588 | Jul. 9, 1991 | Yock, et al. | Laser catheter with imaging capability |
| U.S. Pat. No. 5,181,514 | Jan. 26, 1993 | Solomon, et al. | Transducer positioning system |
| U.S. Pat. No. 5,343,865 | Sep. 6, 1994 | Gardineer, et al. | Apparatus and method for locating an interventional medical device with a ultrasound color imaging system |
| U.S. Pat. No. 5,515,853 | May 14, 1996 | Smith, et al. | Three-dimensional digital ultrasound tracking system |
| U.S. Pat. No. 5,797,849 | Aug. 25, 1998 | Vesely, et al. | Method for carrying out a medical procedure using a three-dimensional tracking and imaging system |
| U.S. Pat. No. 5,876,345 | Mar. 2, 1999 | Eaton, et al. | Ultrasonic catheter, system and method for two dimensional imaging or three-dimensional reconstruction |
| U.S. Pat. No. 6,216,027 | Apr. 10, 2001 | Willis, et al. | System for electrode localization using ultrasound |
| U.S. Pat. No. 6,515,657 | Feb. 4, 2003 | Zanelli | Ultrasonic imager |
| U.S. Pat. No. 6,773,402 | Aug. 10, 2004 | Govari, et al. | Location sensing with real-time ultrasound imaging |
| U.S. Pat. No. 7,529,393 | May 5, 2009 | Peszynski, et al. | Guidance of invasive medical devices by wide view three dimensional ultrasonic imaging |
| U.S. Pat. No. 7,604,601 | Oct. 20, 2009 | Altmann, et al. | Display of catheter tip with beam direction for ultrasound system |
| U.S. Pat. No. 7,930,014 | Apr. 19, 2011 | Huennekens, et al. | Vascular image co-registration |
| U.S. Pat. No. 8,303,509 | Nov. 6, 2012 | Webler, et al. | Echogenic needle catheter configured to produce an improved ultrasound image |
| U.S. Pat. No. 8,412,307 | Apr. 2, 2013 | Willis, et al. | System and method for marking an anatomical structure in three-dimensional coordinate system |
| U.S. Pat. No. 8,428,690 | Apr. 23, 2013 | Li et al. | Intracardiac echocardiography image reconstruction in combination with position tracking system |
| U.S. Pat. No. 8,864,675 | Oct. 21, 2014 | Dietz, et al. | Catheter |
| U.S. Pat. No. 8,900,151 | Dec. 2, 2014 | Ridley, et al. | Ultrasound guided probe device and method of using same |
| U.S. Pat. No. 8,938,283 | Jan. 20, 2015 | Zentgraf, et al | Surgical navigation for repair of heart valve leaflets |
| EP 0617922 A1 | Oct 5, 1994 | Armin Bollinger | Doppler ultrasound probe with needle guide |
| JPH1057376 | Mar. 3, 1998 | SHIMAZAKI TORU | STAB NEEDLE POSITION DETECTION METHOD, STAB NEEDLE VIBRATING DEVICE, VIBRATING LIQUID INJECTION DEVICE AND ULTROSONOGRAPH |
| JPH06205776 | Jul. 26, 1994 | SATO TAKESHI | ULTRASONIC DIAGNOSTIC SYSTEM |

NON-PATENT CITATIONS

Oshiro, O.; Nambu, M.; Matani, A.; Chihara, K., "3D Heart Imaging System Using Echocardiogram and a Digitizer for a US Probe Location", Medical Imaging Technology, vol. 17, No. 2, (March 1999) pp. 165-171.

Stoll, Jeffrey et al; "Passive Markers for Ultrasound Tracking of Surgical Instruments"; J. Duncan and G. Gerig (Eds.): Miccai 2005, LNCS 3750, pp. 41-48, 2005. COPYRGT. Springer-Verlag Berlin Heidelberg 2005; 8 pgs. cited by applicant.

FIELD OF THE INVENTION

This invention relates to an improved ultrasonic probe with additional ultrasonic tracking sensors in order to detect markers in deep region. It is used to identify three-dimensional (3D) catheter position relative to anatomic structure from real-time echo images in cardiac and vascular procedures inside a human body. Both the catheter position and anatomic echo images are updated in the 3D space.

BACKGROUND OF THE INVENTION

Ultrasonic imaging devices are widely used to make internal organs visible in hospitals. However, a catheter inside body cavities cannot be well seen due to sound attenuation and small reflection from the catheter. Many efforts have been made in this field.

U.S. Pat. No. 8,938,283 to Zentgraf et al, which is incorporated herein for reference, describes a technique capable of providing a 3D context for transesophogeal echocardiography data. It consists of a 3D tracking system and an ultrasonic imaging system. A position sensor is embedded inside the ultrasonic probe. U.S. Pat. No. 8,870,779 to Altmann et al, which is incorporated herein for reference, describes a medical imaging system for imaging a patient's body. The system includes a catheter comprising an electrical position sensor and an ultrasonic imaging sensor. In both systems, the position sensors are different from the present invention.

U.S. Pat. No. 8,412,307 to Willis et al and U.S. Pat. No. 6,216,027 to Willis et al, which is incorporated herein for reference, describes an invention to use several ultrasonic transducers inside a heart to establish a fixed 3D coordination system. The system is used in the heart to help the physician guide mapping catheters. U.S. Pat. No. 6,773,402 to Govari et al, which is incorporated herein for reference, describes an invention to use a series of ultrasonic transducers embedded along a catheter for 3D imaging of a heart. The apparatus is for mapping a surface of a cavity within a body. U.S. Pat. No. 6,773,402 to Govari et al, which is incorporated herein for reference, describes an ultrasonic catheter having at least two ultrasonic arrays. The device provides an outline of the heart chamber. Each of the foresaid catheter systems works alone and does not combine a base imaging system as in the present invention.

U.S. Pat. No. 6,515,657 to Zanelli et al, which is incorporated herein for reference, describes an ultrasound imaging system superimposes sectional views created from volumetric ultrasound data and the location data for an intervention device. However, it does not provide details on what kind of catheter to use or whether an active excitation to apply to it.

U.S. Pat. No. 5,343,865 to Gardineer et al, which is incorporated herein for reference, describes an apparatus and method for locating an interventional medical device with an ultrasound color imaging system. The catheter/needle is vibrating and its position is shown as a color image on the conventional color ultrasound display. The present invention takes use of active ultrasound signals instead of vibrations.

U.S. Pat. No. 8,303,509 to Webler et al, which is incorporated herein for reference, describes a catheter having a spherical distal tip to improve its ultrasonic image. Here the passive echo is different from an active signal in the present invention.

U.S. Pat. No. 5,797,849 to Vesely et al, which is incorporated herein for reference, describes a method for carrying out a medical procedure using a 3-D tracking and imaging system. A number of pairs of ultrasonic transducers are employed to track the position of a surgical instrument. The real-time position is provided for an imaging modality system such as a fluoroscope, MRI, CT or ultrasonic device. However, it does not teach details whether and how to configure the modality system.

U.S. Pat. No. 8,900,155 to Ridley et al, which is incorporated herein for reference, describes a method to use an ultrasound catheter with sterile seal to generate the virtual catheter overlay on a sonogram. Since the focus plane of sonogram has some thickness, the actual 3D position of the catheter cannot be easily indicated.

U.S. Pat. No. 5,515,853 to Smith et al, which is incorporated herein for reference, describes a 3-D ultrasound tracking system based on triangulation. However, using a series of transducers contained in a chest harness around a patient looks not a convenient setup for a surgery procedure.

Although many methods have been developed, it remains challenging to find a simple and suitable solution in tracking the catheter position inside body. For example, some physician employ ultrasonic device to assist the procedure of Transcatheter Aortic Valve Implantation (TAVI) to remedy aortic stenosis. Although the nature aortic valve can show on the sonogram, the catheter and the replaceable new valve cannot be easily seen. Contrast dye needs be injected into heart to check both positions under fluoroscope. As we know, the X ray exposure and contrast dye are not good to human body. If a simple ultrasonic probe device can display both the nature valve and catheter on the echocardiography image, it will improve the TAVI procedure significantly.

A conventional ultrasonic probe detects sound reflection and scattering to generate sonographic imaging. However, for an object in a deep position such as a catheter tip, the passive reflected sound signal is weak so its image is not clear. The present invention creates active sound signals from such a deep object so it is easier to be detected by the probe transducers.

On the other hand, the conventional ultrasonic probe can only detect objects within its focus plane of limited thickness. It is a great benefit if it can detect the catheter object earlier when it is far away from the focus plane. To accomplish this, the present invention employs 4 separate ultrasonic sensors located at each corner inside the probe head.

SUMMARY OF THE INVENTION

This invention presents an improved version of an ultrasonic probe by adding more sensors to its head containing transducer array. With the new ultrasound sensors, the probe can detect the 3D location of a catheter and is able to display both the ultrasound anatomic images and the catheter position in real-time. Both the catheter position and anatomic echo images are updated in the 3D space.

In a preferred embodiment of the present invention, a transesophageal echocardiogram (TEE) probe comprises of general transducers and four separate ultrasonic receivers located at each corner of the probe transducer array. A catheter has 4 ultrasonic transmitters embedded at its distal end, each of which can actively send ultrasound signals sequentially. While the TEE probe is updating its 2D imaging, it detects the 3D location of the catheter distal end according to the triangulation principle. The catheter distal end position is rendered in 3-dimensional space relative to the probe echo coordinate system.

In another embodiment, four ultrasonic receivers are embedded at each corner of a conventional transthoracic echocardiogram (TTE) probe. It also detects the position of a catheter equipped with a transmitter inside body cavities. It works in a similar way as foresaid TEE embodiments.

Using the active ultrasound signals, the round trip path of ultrasound echo becomes a one-way trip. The detectable depth can be doubled due to only half length of the attenuation path, which is a good improvement over conventional echo images considering the significant human tissue attenuation.

The catheter 3D position is relative to the 3D coordinate system whose origin is the center of the probe transducer array. As the probe moves inside human body, the 3D coordinate system moves accordingly. The advantage of the present invention is that the echo and catheter position is independent of patient position and orientation. During the procedure, both the patient and the ultrasonic probe are allowed to change position and orientation freely.

DETAILED DESCRIPTION

The present invention is to improve a conventional ultrasonic probe with a tracking ability. Because the passive reflecting signals from a deep internal object emitted by the probe transducers are usually weak, an active ultrasonic transmitter is employed instead so that the probe is able to detect stronger ultrasound signals.

Figure 1:
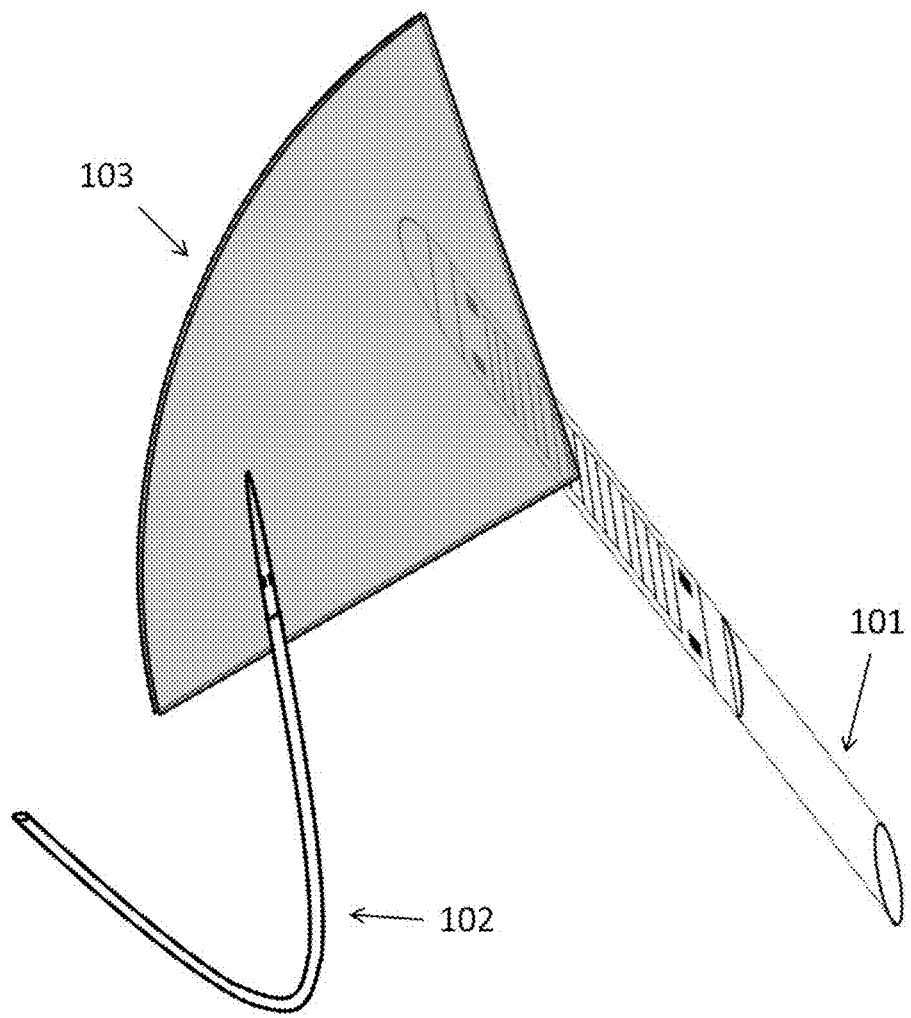
FIG. 1 illustrates the setup of the new tracking probe and a catheter according to one embodiment of the present invention. It also shows the 2D image sector in 3D space.

FIG. 1 shows the setup of the new tracking probe and a catheter according to one embodiment of the present invention. Probe 101 includes 4 additional ultrasound receivers. Catheter 102 also has ultrasound transmitters embedded at its distal end. During operations, probe transducers transmit normal ultrasonic signals and detect echoes to update the 2D anatomic images of internal organs. Within each scanning cycle, one of the catheter transmitters sends an active ultrasonic pulse, which will be detected by the 4 tracking sensors insider probe head. According to the travel time of the pulse, 4 distances from the transmitter to each sensor can be calculated by the system. The 3D position of catheter transmitter relative to the echogram coordinate system can be determined by the triangulation principle. Both the 2D echo graph and the catheter transmitter position are displayed in the 3D space 103.

Since a time division scheme is used for the active ultrasonic signals, the frequency of the 4 ultrasound receivers can be chosen to be the same or different from the probe transducer array frequency. To detect a catheter in a deeper region, a lower frequency is selected. To separate the active transmitting signal from passive reflecting of internal organs, the catheter transmitter ought to use relatively stronger pulse.

Due to a single way to travel for the active ultrasonic signals, the detecting depth can be doubled compared with a conventional round-trip echogram.

In each scanning cycle, four distances are detected by the 4 sensors from one catheter transmitter, only there are needed to determine the transmitter 3D position by the triangulation principle. The $4^{th}$ distance can be combined to any other two distances to repeat triangulation calculation. The average of the 3D positions can improve the detection location precision.

Although the embodiment of a 2D ultrasonic probe is provided here, it can be extended to 3D (or 4D with a time dimension) ultrasonic probe.

Figure 2:
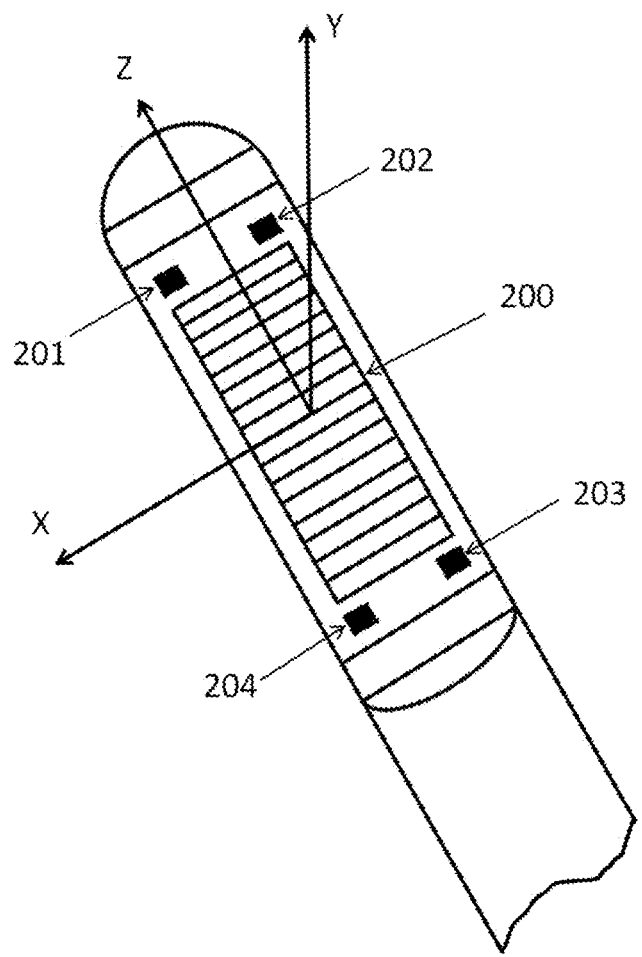
FIG. 2 illustrates the new probe with tracking sensors according to one embodiment of the present invention.

FIG. 2 illustrates the new probe with tracking sensors (201, 202, 203, and 204, respectively) according to one embodiment of the present invention. The main ultrasonic transducer array 200 is inside the probe head as described in U.S. Pat. No. 5,181,514. The 4 tracking sensors are located symmetrically at each corner of the primary transducer array so that the resulting 3D space coordinate origin is at the center of the primary array. The X, Y and Z axis are shown in the figure. It is obvious that the 3D coordinate system is changing with the probe position and orientation.

For another embodiment of a TTE probe system, the setup of the tracking sensors also applies except the TTE probe usually has more transmitter elements and used outside human body.

Figure 3:
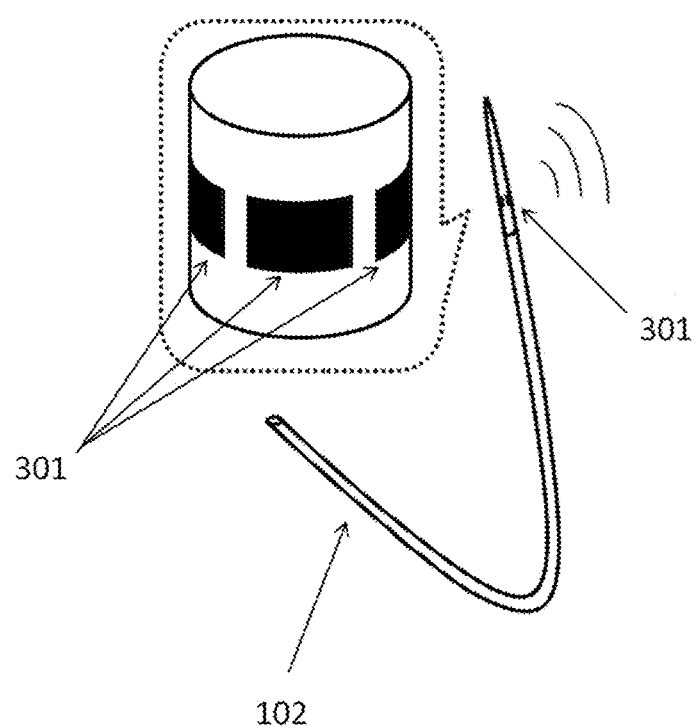
FIG. 3 illustrates the catheter with 4 embedded ultrasonic transmitters evenly surrounding its outer surface.

FIG. 3 is a catheter with ultrasonic transmitters 301 at its distal end. Here 4 ultrasound transmitters are embedded around the catheter to so that at least one will face towards the probe sensors. This way eliminates the need to roll the catheter in order to face the transmitting signal to the receivers. In each scanning cycle, each of the 4 transmitters is excited sequentially and the one with the strongest signal is used for location detection. To achieve a better precision, the catheter diameter is less than one millimeter.

The piezoelectric transducer frequency of each catheter transmitter should be the same as that of the probe sensors.

Figure 4:
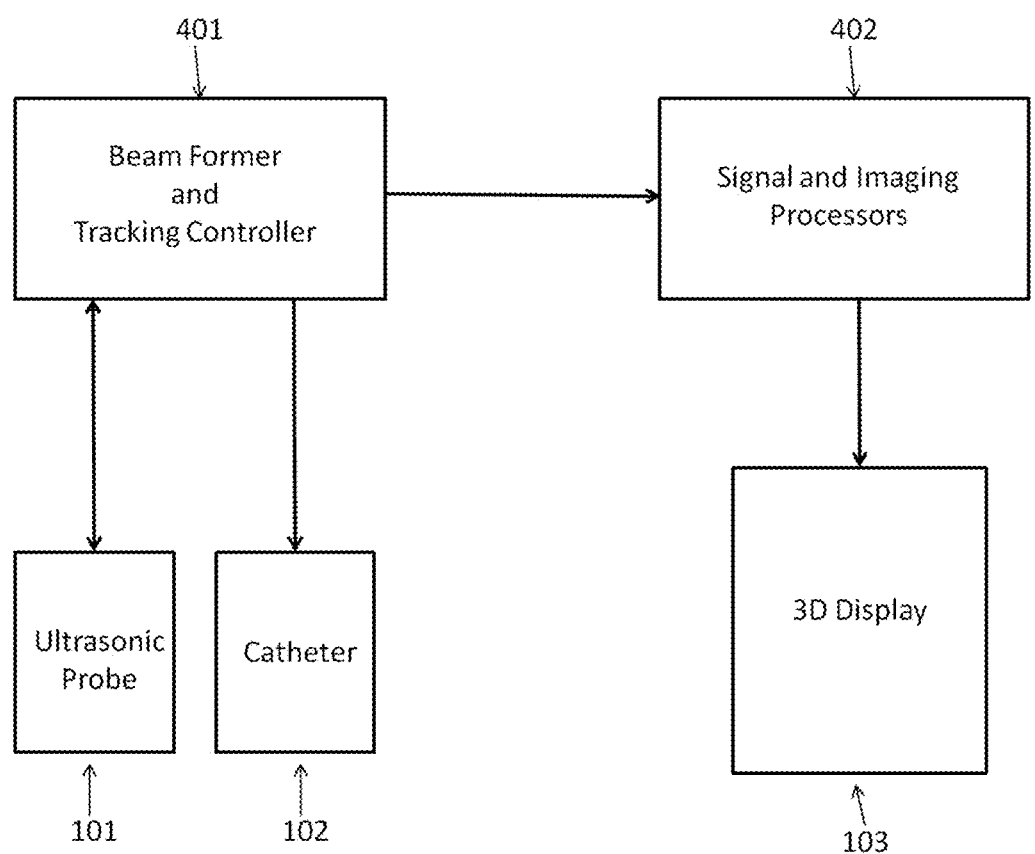
FIG. 4 shows the overall system structure, which is based on a generic ultrasonic instrument.

FIG. 4 shows the overall system configuration. It physically has a similar structure as a general ultrasound device. The only addition is the ultrasonic catheter to be detected. Compared to other tracking systems using sophisticated electronic, magnetic, or optic signals, the present invention provides a much simpler structure and can be easily operated in the surgery environments.

The invention claimed is:

1. A transesophageal ultrasonic system for both imaging and tracking a target catheter while moving freely inside a human body, the ultrasonic system comprising;
   a transesophageal echocardiogram (TEE) tracking probe with head that has a cylindrical cavity housing and a planar top surface;
   an ultrasonic transducer array positioned in the cavity housing; and
   four ultrasonic receiving sensors secured in the planar top surface; and wherein each of the four ultrasonic receiving sensors is located at a respective corner of the ultrasonic transducer array and the four ultrasonic receiving sensors are symmetric with respect to center of the ultrasonic transducer array so that the origin of a three-dimensional tracking coordinate is at the center of the ultrasonic transducer array;
   the target catheter comprising;
   four embedded ultrasound transmitters surrounding an outer surface at a distal end of the catheter, and wherein each of the four embedded ultrasound transmitters sends active signals sequentially to be detected by the four ultrasonic receiving sensors; and
   are electronic processing unit comprising:
   a beam former and one or more signal and imaging processors;
   wherein the TEE probe detects passive echo signals with its transducer array and tracks the catheter with the four receiving sensors by detecting active signals sent out sequentially by the four embedded ultrasound transmitters and from the passive and active signals the three-dimensional catheter position is determined and displayed in the context of the two-dimensional echo age.

2. The ultrasonic system of claim 1, wherein the four embedded ultrasound transmitters are evenly distributed along a circumference surrounding the outer surface at the distal end of the catheter and the diameter of the catheter is less than one millimeter.

3. The ultrasonic system of claim 2, wherein each of the four embedded ultrasound transmitters is excited sequentially and a selected one of the four embedded ultrasound transmitters with the strongest signal is used for location detection during a scanning cycle.

4. The ultrasonic system of claim 1, wherein a three-dimensional position of the catheter are displayed in the context of a two-dimensional echo graph in an image of the three-dimensional space.

5. The ultrasonic system of claim 4, wherein the tracking TEE probe is configured to move inside the esophagus and gastric channel, scan the heart and generate echocardiograms, detect the three-dimensional position of the catheter in the context of said echo image inside the human body.

6. A method of using the ultrasonic system of claim 1, the method comprising the step of moving the tracking TEE probe inside the esophagus and gastric channel, scanning the heart and generating echocardiography images, detecting the three-dimensional position of the catheter inside the human body and displaying the three-dimensional tracking position in the context of echo images.

* * * * *